United States Patent [19]
Gant

[11] Patent Number: 6,083,956
[45] Date of Patent: Jul. 4, 2000

[54] OPTICALLY PURE ANDROGEN MEDIATOR

[75] Inventor: Thomas George Gant, Niantic, Conn.

[73] Assignee: Pfizer Inc., New York, N.Y.

[21] Appl. No.: 09/414,241

[22] Filed: Oct. 7, 1999

Related U.S. Application Data

[60] Provisional application No. 60/109,277, Nov. 20, 1998.
[51] Int. Cl.⁷ ................. A61K 31/47; C07D 491/052
[52] U.S. Cl. ............................... 514/291; 546/89
[58] Field of Search ................. 546/89; 514/291

[56] References Cited

U.S. PATENT DOCUMENTS 5,696,130  12/1997  Jones et al. .................. 514/291

OTHER PUBLICATIONS

Ronald M. Evans, "The Steriod and Thyroid Hormone Receptor Superfamily", Science, vol. 240, 1988 pp. 889–895.

*Primary Examiner*—Bernard Dentz
*Attorney, Agent, or Firm*—Peter C. Richardson; Gregg C. Benson; A. Dean Olson

[57] ABSTRACT

This invention relates to an optically pure androgen mediator, pharmaceutical compositions containing the stereoisomer and the use of the stereoisomer to aid in the prevention and restoration of for example, age-related decline in muscle mass and strength and the treatment of conditions which present with low bone mass in mammals, including humans.

10 Claims, No Drawings

OPTICALLY PURE ANDROGEN MEDIATOR

This application claims priority from provisional application U.S. Ser. No. 60/109,277, filed Nov. 20, 1998, the benefit of which is hereby claimed under 37 C.F.R. §1.78(a)(3).

BACKGROUND OF THE INVENTION

This invention relates to an optically pure androgen mediator, pharmaceutical compositions containing the stereoisomer and the use of the stereoisomer to aid in the prevention and restoration of, for example, age-related decline in muscle mass and strength and the treatment of conditions which present with low bone mass in mammals, including humans.

The worldwide population over 65 years of age is the most rapidly expanding segment of the population. A significant problem for the elderly is the decline in muscle mass and strength leading to frailty, the loss of independence, and eventual institutionalization. In the U.S. today, 1.5 million persons aged 65+ years are institutionalized and 33% of these individuals are put into long term healthcare facilities solely due to their physical frailty and their inability to maintain perquisite activities of daily living. The frail elderly are in need of a therapy either to prevent or restore the loss of age-related muscle mass and strength. There are no therapies currently approved for the treatment of frailty. Further, the only option available to the physician is androgen replacement therapy, but its non-selective tissue action has resulted in many unacceptable side effects.

Concomitant with the age-related decline in muscle mass and strength is the loss of bone mass. Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated.

The elderly are at greatest risk of osteoporosis, and the problem is therefore predicted to increase significantly with the aging of the population. worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

There are currently two main types of pharmaceutical therapy for the treatment of osteoporosis. The first is the use of anti-resorptive compounds to reduce the resorption of bone tissue.

A second type of pharmaceutical therapy for the treatment of osteoporosis is the use of anabolic agents to promote bone formation and increase bone mass. This class of agents is expected to restore bone to the established osteoporotic skeleton.

Intracellular receptors (IRs) form a class of structurally-related genetic regulators scientists have named "ligand dependent transcription factors." (R. M. Evans, 240 Science, 889 1988). Steroid receptors are a recognized subset of the IRs, including the androgen receptor (AR). Regulation of a gene by such factors requires both the IR itself and a corresponding ligand which has the ability to selectively bind to the IR in a way that affects gene transcription.

U.S. Pat. No. 5,696,130 discloses certain tricyclic non-steroidal compounds which are modulators for steroid receptors. The androgen receptor mediator compounds of the '130 patent are disclosed as useful for the treatment of, for example, muscle wasting. One compound disclosed is compound no. 414 (Example 314) R/S-4-Ethyl-1,2,3,4-tetrahydro-6-trifluoromethyl-8-pyranono[5,6-g]quinoline.

SUMMARY OF THE INVENTION

This invention is directed to a compound of Formula I

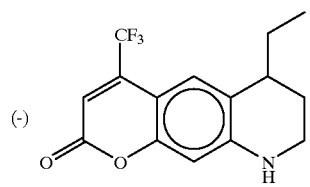

or a pharmaceutically acceptable salt of said compound.

Preferably the compound of Formula I is the free base.

Yet another aspect of this invention is directed to methods for treating wasting diseases in a mammal (including a human being, either male or female) which comprise administering to a mammal in need of such treatment a wasting disease treating amount of a Formula I compound or a pharmaceutically acceptable salt of said compound.

Yet another aspect of this invention is directed to methods for the prevention and/or restoration of the age-related decline in muscle mass and strength in a mammal (including a human being) which comprise administering to a mammal in need of such treatment a therapeutically effective amount of a Formula I compound or a pharmaceutically acceptable salt of said compound.

Yet another aspect of this invention is directed to methods for treating frailty in a mammal (including a human being) which comprises administering to a mammal in need of such treatment a frailty treating amount of a Formula I compound or a pharmaceutically acceptable salt of said compound.

Yet another aspect of this invention is directed to methods for treating acne in a mammal (including a human being) which comprise administering to a mammal in need of such treatment an acne treating amount of a Formula I compound or a pharmaceutically acceptable salt of said compound.

Yet another aspect of this invention is directed to methods for treating male-pattern baldness in a human being which comprise administering to a human in need of such treatment a male-pattern baldness treating amount of a Formula I compound or a pharmaceutically acceptable salt of said compound.

Yet another aspect of this invention is directed to methods for treating male hormone deficiency in a mammal (including a human being) which comprise administering to a mammal in need of such treatment a male hormone deficiency treating amount of a Formula I compound or a pharmaceutically acceptable salt of said compound.

Yet another aspect of this invention is directed to methods for treating hirsutism in a mammal (including a human being) which comprise administering to a mammal in need of such treatment a hirsutism treating amount of a Formula I compound or a pharmaceutically acceptable salt of said compound.

Yet another aspect of this invention is directed to methods for treating hematopoiesis in a mammal (including a human being) which comprise administering to a mammal in need of such treatment a hematopoiesis treating amount of a Formula I compound or a pharmaceutically acceptable salt of said compound.

Yet another aspect of this invention is directed to methods for treating hypogonadism in a mammal (including a human being) which comprise administering to a mammal in need of such treatment a hypogonadism treating amount of a Formula I compound or a pharmaceutically acceptable salt of said compound.

Yet another aspect of this invention is directed to method for treating prostatic hyperplasia in a mammal (including a human being) which comprise administering to a mammal in need of such treatment a prostatic hyperplasia treating amount of a Formula I compound or a pharmaceutically acceptable salt of said compound.

Yet another aspect of this invention is directed to methods for treating hormone dependent cancers in a mammal (including a human being) which comprise administering to a mammal in need of such treatment a hormone dependent cancer treating amount of a Formula I compound or a pharmaceutically acceptable salt of said compound.

Yet another aspect of this invention is directed to methods for treating prostate cancer in a mammal (including a human being) which comprise administering to a mammal in need of such treatment a prostate cancer treating amount of a Formula I compound or a pharmaceutically acceptable salt of said compound.

Yet another aspect of this invention is directed to methods for treating breast cancer in a mammal (including a human being) which comprise administering to a mammal in need of such treatment a breast cancer treating amount of a Formula I compound or a pharmaceutically acceptable salt of said compound.

Yet another aspect of this invention is directed to methods for promoting anabolic activity in a mammal (including a human being) which comprise administering to a mammal in need of such treatment an anabolic promoting amount of a Formula I compound or a pharmaceutically acceptable salt of said compound.

Yet another aspect of this invention is directed to methods for treating obesity in a mammal (including a human being) which comprise administering to a mammal in need of such treatment an obesity treating amount of a Formula I compound or a pharmaceutically acceptable salt of said compound.

Yet another aspect of this invention is directed to methods for treating osteoporosis in a mammal (including a human being) which comprise administering to a mammal in need of such treatment an osteoporosis treating amount of a Formula I compound or a pharmaceutically acceptable salt of said compound.

It is preferred that the mammal is a human.

A preferred dosage is about 0.001 to 100 mg/kg/day of a Formula I compound or a pharmaceutically acceptable salt of said compound.

An especially preferred dosage is about 0.01 to 10 mg/kg/day of a Formula I compound or a pharmaceutically acceptable salt of said compound.

This invention is also directed to pharmaceutical compositions which comprise a therapeutically effective amount of a compound of Formula I or a pharmaceutically acceptable salt of said compound and a pharmaceutically acceptable vehicle, diluent or carrier.

This invention is also directed to pharmaceutical compositions for the treatment of wasting diseases in a mammal (including a human being) which comprise a wasting disease treating amount of a compound of Formula I or a pharmaceutically acceptable salt of said compound and a pharmaceutically acceptable vehicle, diluent or carrier.

This invention is also directed to pharmaceutical compositions for the prevention and/or restoration of the age-related decline in muscle mass and strength in a mammal (including a human being) which comprise a therapeutically effective amount of a compound of Formula I or a pharmaceutically acceptable salt of said compound and a pharmaceutically acceptable vehicle, diluent or carrier.

This invention is also directed to pharmaceutical compositions for the treatment of frailty in a mammal (including a human being) which comprise a frailty treating amount of a compound of Formula I or a pharmaceutically acceptable salt of said compound and a pharmaceutically acceptable vehicle, diluent or carrier.

This invention is also directed to pharmaceutical compositions for the treatment of acne in a mammal (including a human being) which comprise an acne treating amount of a compound of Formula I or a pharmaceutically acceptable salt of said compound and a pharmaceutically acceptable vehicle, diluent or carrier.

This invention is also directed to pharmaceutical compositions for the treatment of male-pattern baldness in a human being which comprise a male-pattern baldness treating amount of a compound of Formula I or a pharmaceutically acceptable salt of said compound and a pharmaceutically acceptable vehicle, diluent or carrier.

This invention is also directed to pharmaceutical compositions for the treatment of male hormone deficiency in a mammal (including a human being) which comprise a male hormone deficiency treating amount of a compound of Formula I or a pharmaceutically acceptable salt of said compound and a pharmaceutically acceptable vehicle, diluent or carrier.

This invention is also directed to pharmaceutical compositions for the treatment of hirsutism in a mammal (including a human being) which comprise a hirsutism disease treating amount of a compound of Formula I or a pharmaceutically acceptable salt of said compound and a pharmaceutically acceptable vehicle, diluent or carrier.

This invention is also directed to pharmaceutical compositions for the stimulation of hematopoiesis in a mammal (including a human being) which comprise a hematopoiesis stimulating treating amount of a compound of Formula I or a pharmaceutically acceptable salt of said compound and a pharmaceutically acceptable vehicle, diluent or carrier.

This invention is also directed to pharmaceutical compositions for the treatment of hypogonadism in a mammal (including a human being) which comprise a hypogonadism treating amount of a compound of Formula I or a pharmaceutically acceptable salt of said compound and a pharmaceutically acceptable vehicle, diluent or carrier.

This invention is also directed to pharmaceutical compositions for the treatment of prostatic hyperplasia in a mammal (including a human being) which comprise a prostatic hyperplasia treating amount of a compound of Formula I or a pharmaceutically acceptable salt of said compound and a pharmaceutically acceptable vehicle, diluent or carrier.

This invention is also directed to pharmaceutical compositions for the treatment of hormone dependent cancer in a mammal (including a human being) which comprise a hormone dependent cancer treating amount of a compound of Formula I or a pharmaceutically acceptable salt of said compound and a pharmaceutically acceptable vehicle, diluent or carrier.

This invention is also directed to pharmaceutical compositions for the treatment of prostate cancer in a mammal (including a human being) which comprise a prostate cancer treating amount of a compound of Formula I or a pharmaceutically acceptable salt of said compound and a pharmaceutically acceptable vehicle, diluent or carrier.

This invention is also directed to pharmaceutical compositions for the treatment of breast cancer in a mammal (including a human being) which comprise a breast cancer treating amount of a compound of Formula I or a pharmaceutically acceptable salt of said compound and a pharmaceutically acceptable vehicle, diluent or carrier.

This invention is also directed to pharmaceutical compositions for the promotion of anabolic activity in a mammal (including a human being) which comprise an anabolic activity promoting amount of a compound of Formula I or a pharmaceutically acceptable salt of said compound and a pharmaceutically acceptable vehicle, diluent or carrier.

This invention is also directed to pharmaceutical compositions for the treatment of obesity in a mammal (including a human being) which comprise an obesity treating amount of a compound of Formula I or a pharmaceutically acceptable salt of said compound and a pharmaceutically acceptable vehicle, diluent or carrier.

This invention is also directed to pharmaceutical compositions for the treatment of osteoporosis in a mammal (including a human being) which comprise an osteoporosis treating amount of a compound of Formula I or a pharmaceutically acceptable salt of said compound and a pharmaceutically acceptable vehicle, diluent or carrier.

The term "treating", "treat" or "treatment" as used herein includes preventative (e.g., prophylactic) and palliative treatment.

By "pharmaceutically acceptable" is meant the carrier, diluent, excipients, and/or salt must be compatible with the other ingredients of the formulation, and not deleterious to the recipient thereof.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent or a mixture of solvents which does not interact with starting materials, reagents, intermediates or products in a manner which adversely affects the yield of the desired product.

The parenthetical negative or positive sign used herein (e.g., nomenclature) denotes the direction a plane of polarized light is rotated by the particular stereoisomer.

The chemist of ordinary skill will recognize that the compound of this invention will contain one or more atoms which may be in a particular stereochemical or geometric configuration, giving rise to stereoisomers and configurational isomers. All such isomers and mixtures thereof are included in this invention. Hydrates and solvates of the compound of this invention are also included.

It will be recognized that the compounds of this invention can exist in isotopically labelled form, i.e., said compounds may contain one or more atoms containing an atomic mass or mass number different from the atomic mass or mass number usually found in nature. Isotopes of hydrogen, carbon, phosphorous, fluorine and chlorine include H, $^2$H, $^3$H, $^{12}$C, $^{13}$C, $^{14}$C, $^{31}$P, $^{32}$P, $^{32}$S, $^{35}$S, $^{18}$F, $^{19}$F, $^{35}$Cl and $^{36}$Cl, respectively. Compounds of this invention, a prodrug thereof, or a pharmaceutically acceptable salt of said compound or of said prodrug which contain those isotopes and/or other isotopes of other atoms are within the scope of this invention. Tritiated, i.e., $^3$H, and carbon-14, i.e., $^{14}$C, isotopes are particularly preferred for their ease of preparation and detectability. Further, certain deuterated, i.e., $^2$H, compounds may afford advantages with respect to metabolic stability and, hence, may be preferred. Isotopically labelled compounds of Formula I of this invention and prodrugs thereof can generally be prepared by carrying out the procedures disclosed in the Schemes and/or in the Examples and Preparations below by substituting a readily available isotopically labelled reagent for a non-isotopically labelled reagent.

DTT means dithiothreitol. DMSO means dimethyl sulfoxide. EDTA means ethylenediamine tetraacetic acid.

Other features and advantages of this invention will be apparent from this specification and the appendant claims which describe the invention.

DETAILED DESCRIPTION OF THE INVENTION

Racemic 5-ethyl-4-trifluoromethyl-5,6,7,8-tetrahydro-1-oxa-8-aza-anthracen-2-one may be prepared according to procedures described in U.S. Pat. No. 5,696,130, the disclosure of which is hereby incorporated by reference.

Certain processes for the manufacture of the compound of this invention are provided as further features of the invention and are illustrated by the following Example.

EXAMPLE

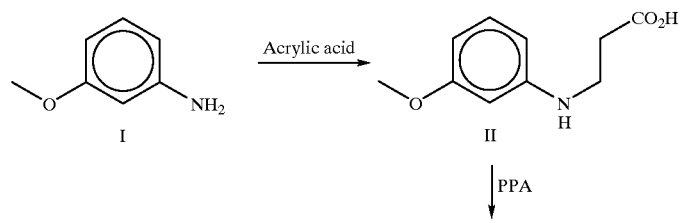

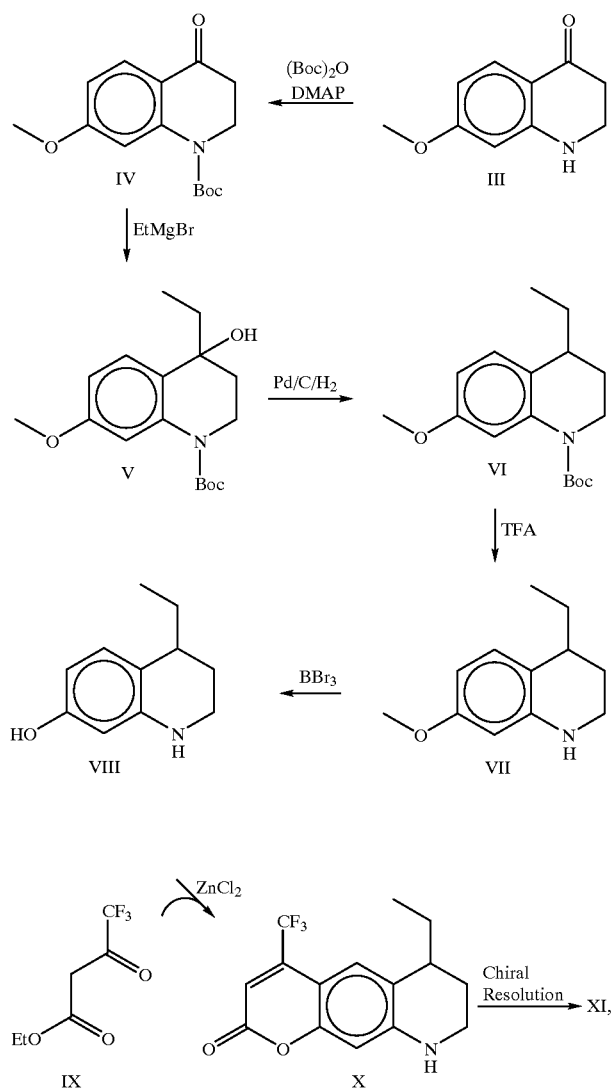

3-(3-Methoxy-phenylamino)-propionic acid (II). To an oven dried 500 mL round bottom flask equipped with a magnetic stir bar and a water cooled reflux condenser was dissolved anisidine (I) (5 mL, 44.6 mmol) in toluene (70 mL). The stirred solution was heated to reflux and acrylic acid (3.0 mL, 44.1 mmol, 1 equiv) was dripped in over a 10 min period. After heating at reflux for 3 h the dark red solution was cooled to room temperature and concentrated in vacuo to remove both the unreacted acrylic acid and toluene to give approximately 9 g of a mixture of the desired amino acid and anisidine as a red viscous oil. The material was immediately used in the next step.

7-Methoxy-2,3-dihydro-1H-quinolin-4-one (III). To an oven dried 500 mL round bottom flask equipped with a magnetic stir bar and a $N_2$ gas inlet, the material obtained above (II) was dissolved in PPA (polyphosphoric acid) (approximately 100 mL). The resulting red viscous solution was heated at 100° C. with constant stirring under a blanket of $N_2$ for 3h. The warm solution was carefully poured into a 1 L beaker with ice (300 g), the contents of the reaction flasked washed into the beaker with a minimal amount of $H_2O$, and the mixture stirred overnight. The solubilized reaction was quenched by slow addition of solid $K_2CO_3$ (bubbling). The product was extracted with $CHCl_3$ (3×150 mL), washed with $H_2O$ (100 mL), dried over $Na_2SO_4$, and concentrated. The solid was purified by flash chromatography (silica gel, $CH_2Cl_2$/MeOH, 99:1) to give 1.69 g (9.54 mmol, 22% over two steps) III as a light yellow solid. Spectral data matched that previously disclosed for this compound.

7-Methoxy-4-oxo-3,4-dihydro-2H-quinoline-1-carboxylic acid tert-butyl ester (IV).

To a flame dried 250 mL round bottom flask equipped with a magnetic stir bar and a $N_2$ gas inlet was added III (1.68 g, 9.48 mmol) and BOC anhydride (2.75 g, 12.6 mmol, 1.33 equiv) in anhydrous THF (80 mL). The solution was cooled to 0° C. and N,N-dimethyl-4-aminopyridine (DMAP) (1.85 g, 15.2 mmol, 1.6 equiv) was added with constant stirring. The mixture was held at 0° C. for 2 days, concentrated, dissolved in a minimal amount of ethyl acetate, and purified via flash chromatography using hexanes/ethyl acetate (4/1) as eluent to afford IV as a white solid (2.3 g, 8.29 mmol, 87%). Spectral data matched that previously disclosed for this compound.

(Rac)-4-Ethyl-4-hydroxy-7-methoxy-3,4-dihydro-2H-quinoline-1-carboxylic acid tert-butyl ester (V). To a flame dried 250 mL round bottom flask equipped with a magnetic stir bar and a $N_2$ gas inlet was added IV (2.23 mg, 8.05 mmol) in dry THF (100 mL). The solution was cooled to 0° C. under a blanket of $N_2$ and a 1.0M solution of ethyl magnesium bromide (EtMgBr) in methyl-tert-butyl ether (16.1 mL, 16.1 mmol, 2 equiv) was added via syringe. The solution was stirred at 0° C. for 1 h. The reaction was quenched with $NH_4Cl$ (saturated aqueous solution) extracted with EtOAc, dried ($MgSO_4$), and concentrated to give V as a colorless oil (1.11 g, 3.61 mmol, 45%). Spectral data matched that previously disclosed for this compound.

(Rac)-4-Ethyl-7-methoxy-3,4-dihydro-2H-quinoline-1-carboxylic acid tert-butyl ester (VI). To an oven dried 250 mL round bottom flask equipped with a magnetic stir bar and a $N_2$ gas inlet was added V (1.11 g, 3.61 mmol) in EtOAc (100 mL). The flask was repeatedly evacuated and flushed with $N_2$ then a catalytic amount of 10% Pd on C (approximately 500 mg) was added. The flask was again evacuated and flushed with $N_2$ several times and then $H_2$ was introduced by Parr shaker at 45 psi and held at that pressure overnight. The flask was again evacuated and flushed with $N_2$ several times to remove any residual $H_2$ and the solution was filtered through a pad of Celite® and concentrated in vacuo to give 907 mg (3.11 mmol, 86%) of the desired amine as a clear colorless oil. Spectral data matched that previously disclosed for this compound.

(Rac)-4-Ethyl-7-methoxy-1,2,3,4-tetrahydro-quinoline (VII). To an oven dried 250 mL round bottom flask equipped with a magnetic stir bar and a $N_2$ gas inlet was added VI (805 mg, 2.76 mmol) in dry $CH_2Cl_2$ (50 mL). To the stirred solution was added TFA (10 mL) at room temperature and was allowed to react for 1 h. The solution was concentrated, quenched with saturated $NaHCO_3$ solution, extracted with $CH_2Cl_2$, the organic layer dried ($MgSO_4$), concentrated, and purified via radial chromatography (4 mm plate) on silica gel using hexanes followed by hexanes/ethyl acetate (20/1) to afford VII as a clear colorless oil (509 mg, 2.66 mmol, 96%). Spectral data matched that previously disclosed for this compound.

(Rac)-4-Ethyl-1,2,3,4-tetrahydro-quinolin-7-ol (VII). In a flame dried 100 mL round bottom flask equipped with a magnetic stir bar and a $N_2$ gas inlet was dissolved VII (509 mg, 2.66 mmol) in $CH_2Cl_2$ (75 mL). The solution was cooled to 0° C. and a 1.0M solution of $BBr_3$ in $CH_2Cl_2$ (7.3 mL, 7.3 mmol, 2.75 equiv) was added dropwise. The solution was warmed to room temperature and stirred overnight under a blanket of $N_2$. The reaction was quenched by addition of saturated $NaHCO_3$ solution, extracted with $CHCl_2$, dried ($MgSO_4$) and concentrated to afford VII as a light yellow oil (452 mg, 2.55 mmol, 96%). Spectral data matched that previously disclosed for this compound.

(Rac)-5-Ethyl-4-trifluoromethyl-5,6,7,8-tetrahydro-1-oxa-8-aza-anthracen-2-one (X). In a oven dried pressure tube equipped with a magnetic stir bar was added VII (292 mg, 1.65 mmol) and TFEM (IX, 6 mL, 25 eq.) and $ZnCl_2$ (6.1 g, 27 equiv.) in absolute EtOH (60 mL). The sealed pressure tube was heated at 100° C. overnight, cooled to room temperature and concentrated. The residue was dissolved in $CHCl_3$, washed with $H_2O$, dried ($MgSO_4$), concentrated, and purified via radial column chromatography (4 mm plate, silica gel) using hexanes/EtOAc (10/1 to 4/1) to give 308 mg (1.04 mmol, 63%) of X as a bright yellow solid. Spectral data matched that previously disclosed for this compound.

(+)-5-Ethyl-4-trifluoromethyl-5,6,7,8-tetrahydro-1-oxa-8-aza-anthracen-2-one (XI). and (−)-5-ethyl-4-trifluoromethyl-5,6,7,8-tetrahydro-1-oxa-8-aza-anthracen-2-one (XII). The racemate, X, was resolved into pure enantiomers (XI) and (XII) on a preparative Chiralcel OD™ column (5 cm×25 cm, 20 micron) using hexanes/isopropyl alcohol/diethylamine (93/7/0.05) as eluent at a flow rate of 50 mL/min. The analytical method was carried out on a Chiralcel OD™ column (4.6 mm×25 cm, 10 micron) using hexanes/isopropyl alcohol/diethylamine (90/10/0.1) as eluent at a flow rate of 1 mL/min. The first-eluted compound, XI, had a retention time of 7.569 minutes on the analytical column, XI: $[\alpha]^{25}d+59°$ (c=1.00, THF). The second-eluted compound, XII, had a retention time of 8.907 minutes on the analytical column, XII: $[\alpha]^{25}d-61°$ (c=0.92, THF).

The starting materials and reagents for the above described Formula I compound, are readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

The Formula I compound of this invention or intermediates in its synthesis have asymmetric carbon atoms. Diasteromeric mixtures can be separated into their individual diastereomers on the basis of their physical chemical differences by methods known per se, for example, by chromatography and/or fractional crystallization. Enantiomers can be separated by, for example, chiral HPLC methods or converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, an enantiomeric mixture of the Formula I compound or an intermediate in its synthesis which contain an acidic or basic moiety may be separated into their corresponding pure enantiomers by forming a diastereomeric salt with an optically pure chiral base or acid (e.g., 1-phenyl-ethyl amine or tartaric acid) and separating the diasteromers by fractional crystallization followed by neutralization to break the salt, thus providing the corresponding pure enantiomers. All such isomers, including diastereomers, enantiomers and mixtures thereof are considered as part of this invention.

More specifically, the Formula I compound of this invention may be obtained in enantiomerically enriched form by resolving the racemate of the final compound or an intermediate in its synthesis (preferably the final compound) employing chromatography (preferably high pressure liquid chromatography [HPLC]) on an asymmetric resin (preferably Chiralcelm AD or OD [obtained from Chiral Technologies, Exton, Pa.]) with a mobile phase consisting of a hydrocarbon (preferably heptane or hexane) containing between 0 and 50% isopropanol (preferably between 2 and 20%) and between 0 and 5% of an alkyl amine (preferably 0.1% of diethylamine). Concentration of the product containing fractions affords the desired materials.

All salts of the Formula I compound are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

In addition, when the Formula I compound of this invention forms hydrates or solvates they are also within the scope of the invention.

The Formula I compound of this invention, and the salts thereof are all adapted to therapeutic use as agents that mediate androgen receptors in mammals, particularly humans. By virtue of this activity, these agents improve frailty and other disease/conditions detailed above.

The utility of the Formula I compound of the invention and the salts thereof as medical agents in the treatment of the above described disease/conditions in mammals (e.g., humans, male or female) is demonstrated by the activity of the compound of this invention in conventional assays and them vitro assay described below. The in vitro assay (with appropriate modifications within the skill in the art) may be used to determine the activity of analogous agents as well as the compounds of this invention. Such assays also provide a means whereby the activities of the Formula I compound of this invention, and the salts thereof can be compared with the activities of other known compounds. The results of these comparisons are useful for determining dosage levels in mammals, including humans, for the treatment of such diseases.

The following protocols can of course be varied by those skilled in the art.

Human Androgen Receptor Binding Analysis

The following is a brief description of the assay that determines the affinity of a compound for the recombinant human androgen receptor (hAR). Competitive binding analysis is performed on baculovirus/Sf9 generated hAR extracts in the presence or absence of differing concentrations of drug and a fixed concentration of $^3$H-dihydrotestosterone ($^3$H-DHT) as tracer. This binding assay method is a modification of a protocol previously described (Chang, et. al. *J. Steroid Biochem.* 20(1):11–17 1984). Briefly, progressively decreasing concentrations of compounds are incubated in the presence of hAR extract (Chang et al. *P.N.A.S.* Vol. 89, pp. 5546–5950, 1992), hydroxylapatite and 1 nM $^3$H-DHT for one hour at 4° C. Subsequently, the binding reactions are washed three times to completely remove excess unbound $^3$H-DHT. hAR bound.

$^3$H-DHT levels are determined in the presence of compounds (=competitive binding) and compared to levels bound when no competitor is present (=maximum binding). Compound binding affinity to the hAR is expressed as the concentration of compound at which one half of the maximum binding is inhibited. The binding data for the racemate and (+) and (−) stereoisomers for 5-ethyl-4-trifluoromethyl-5,6,7,8-tetrahydro-1-oxa-8-aza-anthracen-2-one are provided below.

|  | Racemate (±) | (+) Enantiomer | (−) Enantiomer |
|---|---|---|---|
| hAR Binding IC$_{50}$: | 35 nM | 112 nM | 5 nM |

Administration of the compound of this invention can be via any method which delivers the compound of this invention systemically and/or locally. These methods include oral routes, parenteral, intraduodenal routes, etc. Generally, the compound of this invention is administered orally, but parenteral administration (e.g., intravenous, intramuscular, subcutaneous or intramedullary) may be utilized, for example, where oral administration is inappropriate for the target or where the patient is unable to ingest the drug.

In general an effective dosage for the Formula I compound of this invention and the salts of the compound is in the range of 0.001 to 100 mg/kg/day, preferably 0.01 to 10 mg/kg/day.

Furthermore, it will be understood by those skilled in the art that the compound of the present invention, including pharmaceutical compositions and formulations containing the compound or a salt thereof, can be used in a wide variety of combination therapies to treat the conditions and diseases described above. Thus, the compound or a salt thereof of the present invention can be used in combination with other hormones and other therapies, including, without limitation, chemotherapeutic agents such as cytostatic and cytotoxic agents, immunological modifiers such as interferons. interleukins, growth hormones and other cytokines, hormone therapies, surgery and radiation therapy.

The compound or a salt thereof of the present invention is generally administered in the form of a pharmaceutical composition comprising the compound or a salt thereof of this invention together with a pharmaceutically acceptable vehicle, diluent or carrier. Thus, the compound of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol® or Capmul®, in a soft gelatin capsule. Antioxidants may be added to prevent long term degradation as appropriate. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easter, Pa., 15th Edition (1975).

Pharmaceutical compositions according to the invention may contain 0.1%–95% of the compound or a salt thereof of this invention, preferably 1%–70%. In any event, the composition or formulation to be administered will contain a quantity of a compound or a salt thereof according to the invention in an amount effective to treat the disease/condition of th subject being treated.

The compound or a salt thereof of this invention either alone or in combination with other compounds generally will be administered in a convenient formulation. The following formulation examples only are illustrative and are not intended to limit the scope of the present invention.

In the formulations which follow, "active ingredient" means a compound or a salt thereof of this invention.

Formulation 1: Gelatin Capsules

Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

| Formulation 2: Tablets | |
| --- | --- |
| Ingredient | Quantity (mg/tablet) |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

| Formulation 3: Tablets | |
| --- | --- |
| Ingredient | Quantity (mg/tablet) |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

| Formulation 4: Suspensions | |
| --- | --- |
| Ingredient | Quantity (mg/5 ml) |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume.

| Formulation 5: Aerosol | |
| --- | --- |
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6: Suppositories | |
| --- | --- |
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7: Intravenous Solution | |
| --- | --- |
| Ingredient | Quantity |
| Active ingredient dissolved in ethanol 1% | 20 mg |
| Intralipid ™ emulsion | 1,000 mL |

The solution of the above ingredients is intravenously administered to a patient at a rate of about 1 mL per minute.

Soft gelatin capsules are prepared using the following:

| Formulation 8: Soft Gelatin Capsule with Oil Formulation | |
| --- | --- |
| Ingredient | Quantity (mg/capsule) |
| Active ingredient | 10–500 |
| Olive Oil or Miglyol ® Oil | 500–1000 |

What is claimed is:

1. A substantially free of the (+) isomer compound of Formula I

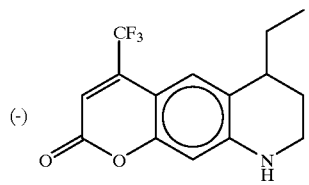

or a pharmaceutically acceptable salt of said compound.

2. The compound of claim 1 wherein said compound is the free base.

3. A method for treating frailty, osteoporosis or a wasting disease in a mammal by administering to a mammal in need of such treatment a therapeutically effective amount of a compound of claim 1, or a pharmaceutically acceptable salt of said compound.

4. A method as recited in claim 3 wherein the mammal is a human.

5. A method as recited in claim 4 wherein osteoporosis is treated.

6. A method as recited in claim 4 wherein a wasting disease is treated.

7. A method as recited in claim 4 wherein frailty is treated.

8. A method as recited in claim 4 wherein the therapeutically effective amount of the compound of claim 1 is about 0.01 mg/kg/day to about 10 mg/kg/day.

9. A pharmaceutical composition which comprises a therapeutically effective amount of a compound of claim 1, or a pharmaceutically acceptable salt of said compound and a pharmaceutically acceptable vehicle, diluent or carrier.

10. A pharmaceutical composition for the treatment of frailty in a mammal which comprises a frailty treating amount of a compound of claim 1, or a pharmaceutically acceptable salt of said compound and a pharmaceutically acceptable vehicle, diluent or carrier.

* * * * *